United States Patent [19]

Dolan et al.

[11] Patent Number: 5,765,576
[45] Date of Patent: Jun. 16, 1998

[54] DENTAL FLOSS ARTICLE AND METHOD OF MAKING SAME

[75] Inventors: John W. Dolan, Boothwyn, Pa.; John W. Spencer, Jr., Rising Sun, Md.; Loretta A. Whelan, Newark, Del.

[73] Assignee: W. L. Gore & Associates, Newark, Del.

[21] Appl. No.: 788,608

[22] Filed: Jan. 24, 1997

Related U.S. Application Data

[63] Continuation of Ser. No. 641,102, Apr. 26, 1996.

[51] Int. Cl.⁶ .................................................. A61C 15/00
[52] U.S. Cl. ........................................ 132/321; 132/323
[58] Field of Search ................................. 132/321, 323, 132/324, 325, 326, 327, 328, 329

[56] References Cited

U.S. PATENT DOCUMENTS

| | | |
|---|---|---|
| 3,699,979 | 10/1972 | Muhler et al. . |
| 3,744,499 | 7/1973 | Wells . |
| 3,771,536 | 11/1973 | Dragan . |
| 3,830,246 | 8/1974 | Gillings . |
| 3,930,059 | 12/1975 | Wells . |
| 3,953,566 | 4/1976 | Gore . |
| 4,008,727 | 2/1977 | Thornton . |
| 4,011,658 | 3/1977 | Tarrson et al. . |
| 4,029,113 | 6/1977 | Guyton . |
| 4,034,763 | 7/1977 | Frazier . |
| 4,034,771 | 7/1977 | Guyton . |
| 4,142,538 | 3/1979 | Thornton . |
| 4,270,556 | 6/1981 | McAllister . |
| 4,280,500 | 7/1981 | Ono . |
| 4,372,293 | 2/1983 | Vijil-Rosales . |
| 4,414,990 | 11/1983 | Yost . |
| 4,450,849 | 5/1984 | Cerceo et al. . |
| 4,693,365 | 9/1987 | Corella . |
| 4,776,358 | 10/1988 | Lorch . |
| 4,832,063 | 5/1989 | Smole ............................. 132/321 |
| 4,836,226 | 6/1989 | Wolak . |
| 4,855,099 | 8/1989 | D'Andolfo et al. ............. 264/103 |
| 4,985,296 | 1/1991 | Mortimer, Jr. . |
| 4,996,056 | 2/1991 | Blass . |
| 4,998,978 | 3/1991 | Varum . |
| 5,033,488 | 7/1991 | Curtis et al. . |
| 5,063,948 | 11/1991 | Lloyd ............................... 132/321 |
| 5,094,255 | 3/1992 | Ringle ............................. 132/321 |
| 5,098,711 | 3/1992 | Hill et al. . |
| 5,209,251 | 5/1993 | Curtis et al. ................... 132/321 |
| 5,220,932 | 6/1993 | Blass . |
| 5,226,434 | 7/1993 | Britton et al. . |
| 5,226,435 | 7/1993 | Shonen et al. . |
| 5,274,074 | 12/1993 | Tang et al. ..................... 528/370 |
| 5,289,836 | 3/1994 | Peng . |
| 5,305,768 | 4/1994 | Gross et al. . |
| 5,320,117 | 6/1994 | Lazzara et al. . |
| 5,340,581 | 8/1994 | Tseng et al. . |
| 5,357,989 | 10/1994 | Gathani . |
| 5,383,904 | 1/1995 | Totakura et al. ............... 606/228 |
| 5,413,127 | 5/1995 | Hill ................................. 132/321 |
| 5,454,834 | 10/1995 | Boebel et al. .................. 606/228 |
| 5,518,012 | 5/1996 | Dolan et al. . |
| 5,566,691 | 10/1996 | Dolan et al. . |

FOREIGN PATENT DOCUMENTS

| | | |
|---|---|---|
| 335466 | 10/1989 | European Pat. Off. . |
| 451729 | 4/1991 | European Pat. Off. . |
| 0 750 902 | 1/1997 | European Pat. Off. . |
| 2128133 | 4/1984 | United Kingdom . |
| 2258402 | 2/1993 | United Kingdom . |
| 9210978 | 9/1992 | WIPO . |
| 9506447 | 3/1995 | WIPO . |
| 9534252 | 12/1995 | WIPO . |
| 96 10478 | 4/1996 | WIPO . |
| 9610478 | 4/1996 | WIPO . |

*Primary Examiner*—Gene Mancene
*Assistant Examiner*—Pedro Philogene
*Attorney, Agent, or Firm*—Victor M. Genco, Jr.

[57] ABSTRACT

The present invention is a floss material defined by a towed filament. The filament may be made from a towed polytetrafluoroethylene material or a towed polymeric material.

15 Claims, 2 Drawing Sheets

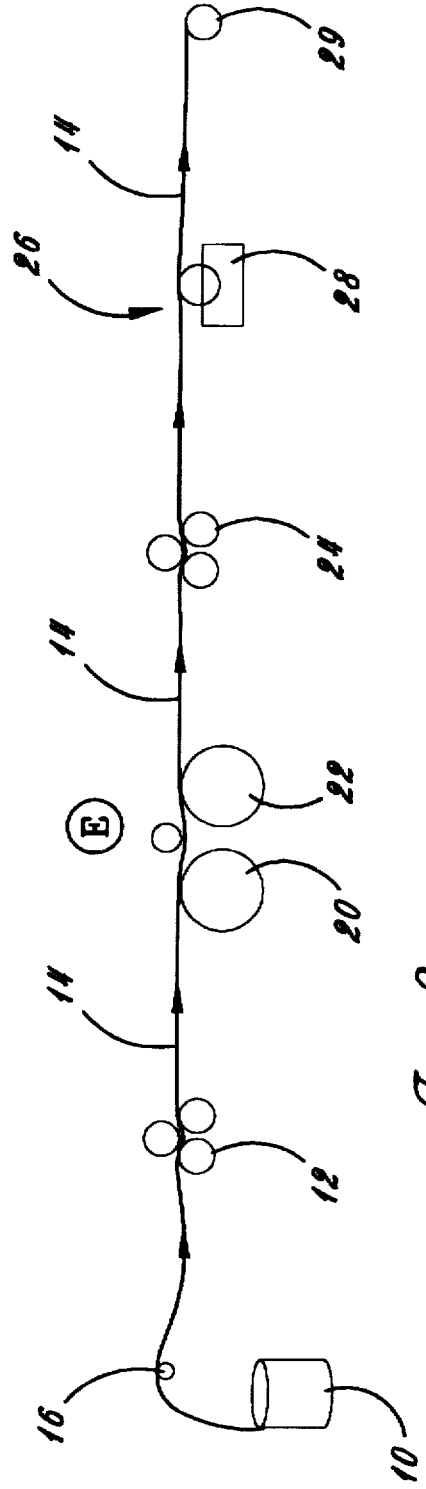
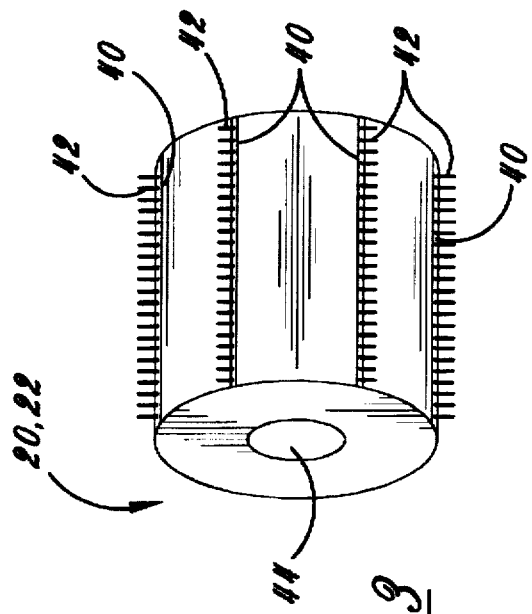

DENTAL FLOSS ARTICLE AND METHOD OF MAKING SAME

CROSS REFERENCE TO RELATED APPLICATION

This application is a continuation of Ser. No. 08/641,102, filed Apr. 26, 1996.

FIELD OF THE INVENTION

The present invention relates to a dental floss article, and particularly to a dental floss article having at least one towed fiber.

BACKGROUND OF THE INVENTION

Flexible fibers made from porous polytetrafluoroethylene (PTFE) have been used for a variety of purposes, such as for a dental floss for example. Embodiments of PTFE dental flosses include: a dental floss folded upon itself to contain active agents (U.S. Pat. No. 4,776,358); microcrystalline wax coated porous PTFE fibers (U.S. Pat. Nos. 5,033,488 and 5,209,251); a non-porous PTFE floss material (U.S. Pat. No. 5,220,932); and a uniform, shred resistant porous PTFE floss material (U.S. Pat. No. 5,518,012). Also, presently, there are a number of commercially available PTFE flosses, including those sold under the trademarks GLIDE® by W. L. Gore & Associates, Inc., COLGATE PRECISION® by Colgate Palmolive Company, and EASY-SLIDE® by Johnson & Johnson Consumer Products, Inc.

Typically, PTFE flosses are formed from a thin, flat tape and are processed into a single filament strand, as compared to conventional nylon flosses which are formed from multiple strands twisted into a fiber with uniform dimensions. PTFE flosses have a number of advantages over conventional nylon flosses, including resistance to shredding (i.e., the breaking off of individual strands of the fiber between teeth of a user), high lubricity which allows for easy sliding between tight dental contacts, and a naturally bright white color which offers a sense of cleanliness.

A shortcoming of PTFE flosses is the high lubricious nature of the material which makes it difficult for an individual to hold the floss during use. Typically, the floss slips between fingers and cannot be tightly grasped, which is frustrating to a user thereof, and which makes flossing ineffective. To address such shortcomings, commercially available PTFE flosses have one or both sides of the floss coated with a material, such as natural beeswax or a microcrystalline wax, for example. Such a coating enhances the grippability of the floss.

A process for applying a coating of wax to a PTFE filament is taught in U.S. Pat. No. 5,220,932. Additionally, materials such as flavorants, medicaments, vitamins, anti-inflammatory agents, and anti-microbial agents are typically added and suspended into a dental floss coating which is then applied or deposited on the surface of the dental floss. As should be understood, it is beneficial for a dental floss of PTFE, or porous PTFE, to contain copious amounts of a material to provide improved grippability as well as increased dosage levels of the added materials.

Conventional PTFE filaments typically are unable to hold sufficient quantities of a coating due to the lubricious property of the PTFE floss material and the minimal surface area thereof. When large amounts of a coating are applied to a conventional flat PTFE filament, the coating unacceptably flakes off either in a users hands or between teeth. One remedy is to provide a folded PTFE material which contains a coating material. This folded design, however, suffers from numerous shortcomings including increased manufacturing cost.

Flaking of a coating does not typically occur with conventional multifilament nylon flosses, as a significant amount of floss surface area is available due to its composition of a collection of multifilaments. However, conventional multifilament nylon flosses suffer from shredding during use. Such shredding occurs as a user passes the floss through a dental contact and one, two, or more of the individual single multifilaments break away. Once a single filament breaks away, it tangles with other filaments thereby increasing the cross-sectional dimension of the floss which results in the floss not being of an appropriate size to permit passage through the dental contact. Fibrillation in dental floss, on the other hand, is distinguished from shredding in that shredding is considered the breaking off of individual strands of the fiber between the teeth. Fibrillation is the splitting of the original fiber to form separate continuous fibers. Both shredding and fibrillation are not desired in a dental floss product.

In addition to the forgoing, present PTFE or porous PTFE floss construction leave the user without an aggressive feel between dental contacts.

The foregoing illustrates limitations known to exist in the present dental flosses. Thus, it is apparent that it would be advantageous to provide an improved dental floss directed to overcoming one or more of the limitations set forth above. Accordingly, a suitable alternative is provided including features more fully disclosed hereinafter.

SUMMARY OF THE INVENTION

The present invention advances the art of dental floss, and the techniques for creating such floss beyond which is known to date. In one aspect of the present invention, a floss material is comprised of a towed filament. An alternate embodiment of the floss material of the present invention includes a dental floss comprised of a filament of a towed porous polytetrafluoroethylene material or a towed polymeric material. The dental floss material of the present invention may have a width of at least about 0.5 mm to about 5 mm and a thickness of at least about 35 μm. The dental floss material of the present invention may further include a coating layer, which may include at least one active agent.

A method of producing the dental floss is also disclosed wherein a monofilament material is towed. Such a towed monofilament material may be a porous polytetrafluoroethylene.

Accordingly, it is a purpose of the present invention to provide a PTFE floss material that is more grippable and easily handled than existing PTFE flosses.

Another purpose of the present invention is to provide a fibrillation resistant dental floss article.

It is a further purpose of the present invention to provide a dental floss article which is operable to deliver a great amount of an active ingredient to a user as compared with a conventional multifilament or monofilament dental floss article.

It is still another purpose of the present invention to provide a PTFE dental floss that has an aggressive feel which is similar to a conventional multifilament nylon dental floss.

The foregoing illustrates limitations known to exist in present dental floss material. Thus, it is apparent that it would be advantageous to provide an improved dental floss directed to overcoming one or more of the limitations set forth above. Accordingly, a suitable alternative is provided including features more fully disclosed hereinafter.

BRIEF DESCRIPTION OF THE DRAWINGS

The foregoing summary, as well as the following detailed description of a preferred embodiment of the present invention, will be better understood when read in conjunction with the appended drawings. For purposes of illustrating the present invention, there is shown in the drawings an embodiment which is presently preferred. It should be understood, however, that the invention is not limited to the precise arrangement and instrumentality shown. In the drawings:

FIG. 2 is a schematic of a process for making the dental floss article of the present invention; and FIG. 3 is a view of a pin wheel used in creating a towed dental floss article in accordance with the present invention.

DETAILED DESCRIPTION OF THE INVENTION

Figure 1:
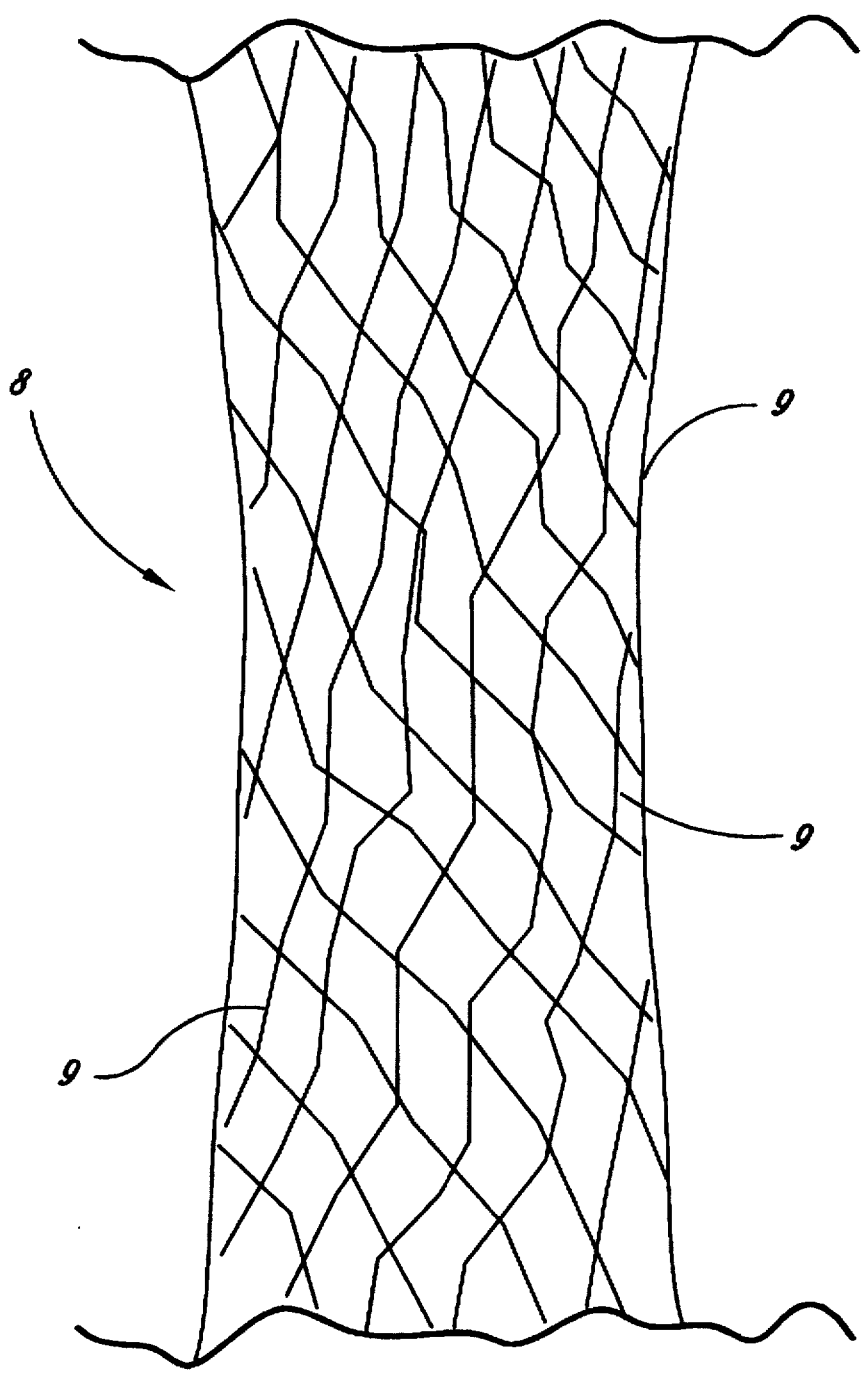
FIG. 1 is a plan view of a towed filament comprising a dental floss article of the present invention.

Referring now to the drawings, wherein similar reference characters designate corresponding parts throughout the several views, the dental floss article of the present invention comprises a towed filament for facilitating oral prophylaxis and is generally illustrated at 8 in FIG. 1. As should be understood, towing is a technique which imparts a multitude of individual, noncontinuous fractures in a matrix of a filament material thereby providing for increased surface area by creating small fibrils or strands 9. The fibrils or strands 9 in such a towed filament are non-continuous. When a strand of such a dental floss article breaks away from the main cross-section of a towed filament, the propagation of the breakage is impeded due to the non-continuous geometry or configuration of the towed filament. If used in oral prophylaxis, such a towed filament is believed to produce a significantly better cleaning action than a conventional PTFE floss.

A preferred embodiment of the present invention is defined by a towed filament made from a porous polytetrafluoroethylene (PTFE) material.

As the term is used herein, porous PTFE shall mean a membrane which may be prepared by any number of known processes, for example, by stretching or drawing processes, by papermaking processes, by processes in which filler materials are incorporated with the PTFE resin and which are subsequently removed to leave a porous structure, or by powder sintering processes. Preferably, the porous PTFE membrane is a porous expanded PTFE membrane having a microstructure of interconnected nodes and fibrils, as described in U.S. Pat. Nos. 3,953,566; 4,187,390; and 4,110, 392, which are incorporated herein by reference, and which fully describe a preferred material and processes for making the same.

As the term is used herein, polymer is understood within the art to include such materials including but not limited to polyolefins, nylons, and fluoropolymers As the term is used herein, dental floss shall mean a thread-like material suitable for use in facilitating oral prophylaxis. Throughout this description, filament and fiber are used interchangeably with the term dental floss.

The dental floss article of the present invention has many improved properties over previous dental floss articles. As seen in FIG. 1, the dental floss article of the present invention maintains uniform dimensions despite the individual, non-continuous strands which define the towed filament of the dental floss article. The dental floss article of the present invention also exhibits increased porosity or "void content" as compared with a conventional monofilament dental floss article. The void content is measured by the ratio of the article's bulk density to its intrinsic density. When processed in the manner described hereinafter, it has been found that the dental floss article of the present invention remains quite porous and compressible in its completed form and has the ability to densify under low stress. This property makes the dental floss easier to handle and more comfortable when applied between teeth and gums.

The towing process of the present invention increases the area of the outer surface of a monofilament material thereby providing for an increased amount of a coating material which may be to be applied to the dental floss article. As the term is used herein, "outer surface" is defined as an unfolded or uncreased surface which can be seen when exposed to ambient light as a towed filament is rotated 360 degrees around the filament's center line which runs along the length of such a filament. Adherence of a coating onto such a filament presents a number of advantages. One such advantage associated with towed filaments of a PTFE material is that such a coating provides a coefficient of friction sufficiently high to permit a user to securely grasp the PTFE floss, but is not so high as to prohibit use of the floss between teeth in tight interproximal dental contacts. Additionally, high quantities of a desired material may be successfully incorporated on and within the inventive dental floss article without the annoyance of the material flaking off. If a natural beeswax is used, wax percentages of 0.5% to 50% by weight are achieved, but preferably 5 to 15% using traditional lick roller, or dip/bathe waxing methods. However, higher percentages such as 20% or greater, are easier achieved using the bath/dip waxing method during a one-pass type operation. High quantities of the desired material are achieved as well using the traditional lick roller method if multiple passes through the lick roller apparatus are performed. It is well known in the art to incorporate other materials for certain enhanced properties, such as flavors or medicines, for example. Hence, it desirable to achieve a sufficient quantity of the desired material by weight within the floss article such that the overall additive concentration is effective. Another advantage is that such a coating material may contain additives and agents which may improve the flossing experience. Coating layers applied to the towed dental floss filament of the present invention may include, but are not limited to waxes, polyvinyl alcohols and polyethyleneoxides.

It has long been a desire to include active ingredients in a dental floss coating to provide a direct topical application to a user's teeth or gums below the gum line. Active ingredients may include, but are not limited to antioxidants, flavor impact agents, sodium fluoride, antimicrobials, antibiotics, antibacterial agents, antifungal agents, remineralizing agents, whitening agents, immunological agents, anti-tartar agents, anti-caries agents, anti-plaque agents, lysozmes, anti-inflammatory agents, homeostatic agents, analgesics, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, othophosphoric acid, monosodium phosphate, monopotassium phosphate, disodium phosphate, dipotassium phosphate, hemisodium phosphate, benzothonium, chloride, acetyl triemethyl ammonium bromide, sanguinaria, triclosan, tetracycline, cety pyridinium chloride, benzothonium chloride, melt emulsion of dimethicone and mixtures thereof. Other materials may be added as well such as natural flavor, natural oils and dyes, for example.

A method for making the dental floss article of the present invention is illustrated in FIG. 2. Spool 10 contains a filament 14, such as a porous PTFE. The filament 14 is removed from spool 10 by a driven tri-roller nip device 12. The filament 14 is guided off the spool 10 using an idler shaft 16 and then pulled across two rotating pin wheels 20, 22 by use of the drive tri-roller nip device 24.

The rotating pin wheels 20, 22 are shown in detail in FIG. 3; pin wheels 20, 22 rotate on respective hubs 44. The major diameter of the wheels, which is the diameter of the wheel without the attached combs, ranges from about 50 to 300 mm and the length of the wheels may range from about 100 to 600 mm. The wheels have a series of combs 40 which contain an array of tapered steel pins 42. The steel pins are about 1 mm in diameter and are separated by a distance of about 1 to 3 mm, preferably 1 mm apart. The number of combs 40 affixed to a pin wheel may vary from about 3 to about 12 individual combs. The length of the tapered steel pins 42 that extends beyond the diameter of the pin wheel 20, 22 is between about 6–30 mm, preferably about 12 mm and tapers into a sharp point.

The surface velocity of the filament 14 is at least 1% less, and preferably is at least 15% less, than the angular velocity of the rotating pin wheels 20, 22. This difference ensures that the steel pins 42 quickly pierce the filament 14 and are removed such to render the filament with non-continuous apertures throughout the matrix and length thereof. As should be understood, the faster the pins 42 enter and exit the filament 14, the smaller and finer the tow structure. The direction of rotation is preferably in the direction of filament motion with respect to the angular rotation of the pin wheels 20, 22. However, a tow pattern can be achieved if the wheels rotate in the opposite direction.

After the towing operation, the filament 14 is then optionally coated by running the filament across a lick roll coater assembly 26. The assembly 26 rotates either with or against the movement of the filament. It is found that the filament 14 picks-up an increased amount of coating when roller 26 rotates in the direction against the filament movement. The roller 26 is partially submerged in a tank 28 containing the coating. The coating is heated to at least its melting temperature, but below its degradation temperature, or below the degradation temperature of any constituent suspended or dissolved in the coating. The process of applying a coating to a fiber is well known in the art and described in U.S. Pat. No. 5,220,932 to Blass herein incorporated by reference. The coating may be applied to the filament by other conventional techniques including, for example, spraying or padding. Suitable coatings may include, but are not limited to microcrystalline wax, natural beeswax, polyvinyl alcohol or polyethyleneoxide.

The coating is air cooled after the coating process. After the coating has cooled, it may then be wound on to spool 29. It is preferred that the filament be maintained in an essentially flat orientation on spool 29.

The filament 14 of the present invention may be formed by any suitable process. In one embodiment of the present invention, the filament may be formed as taught in U.S. Pat. No. 5,518,012, which is incorporated herein by reference.

In another embodiment of the present invention, the filament 14 may be made from a sheet of porous polytetrafluoroethylene made in accordance with U.S. Pat. No. 3,543,566, incorporated herein by reference. In such an embodiment, a preferred sheet has a thickness of about 0.5 to 1.0 mm; a density of about 0.8 to 1.5 g/cc; and a tenacity of about 0.5 to 1.0 g/tex. Each of these properties are measured in a suitable conventional manner. Width and thickness is determined through any conventional means, such as calipers or measurements using a scanning electron microscope. Density is determined by dividing the measured weight of the sample by the computed volume of the sample. The volume is computed by multiplying the measured length, width, and thickness of the sample. Tenacity is calculated by dividing a sample's tensile strength by its normalized weight per unit length [tex(grams/1000 meters) or denier (grams/9000 meters)]. The sheet may then be slit into strands by passing the sheet through a series of gapped blades set about 0.5 to 20 mm apart. After slitting, the filaments may be subjected to a further heat treatment and/or expansion step, such as through the processes discussed below. Finally, the filaments are wound onto a spool with care taken to avoid rolling or folding the filaments during the spooling process.

Preferably, a porous PTFE sheet is formed in the following manner. A fine powder PTFE resin is blended with a lubricant, such as odorless mineral spirits, until a compound is formed. The volume of the lubricant used should be sufficient to lubricate the primary particles of the PTFE resin so to minimize the potential of the shearing of the particles prior to extruding. The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications, a reduction ratio of about 75:1 to 100:1 is preferred. The lubricant may then be removed, such as through volatilization, and the dry coherent extrudate is expanded in at least one direction about 1.1 to 50 times its original length (with about 1.5 to 2.5 times being preferred). Expansion may be accomplished by passing the dry coherent extrudate over a series of rotating heated rollers or heated plates.

Once a sheet material is formed, the sheet may be formed into a filament by slitting the dry coherent expanded extrudate into predetermined widths by passing it between a set of gapped blades or other cutting means. Following cutting, the slit coherent extrudate may then be further expanded in the longitudinal direction at a ratio of about 1:1.1 to 50:1 (with 15:1 to 35:1 being preferred) to form a fiber. Finally, this filament may be subjected to an amorphous locking step by exposing the fiber to a temperature in excess of 342° C.

The width of the fiber can be controlled by several process variables known in the art of expanding PTFE. Variables which can affect the width of the filament are: slit width, expansion temperatures and expansion ratio.

The final dimensions of the fiber prior to the towing operation should comprise: a width of about 0.5 to 5.0 mm; a thickness of about 35 to 250 µm; a weight/length of about 80 to 450 tex; a density of about 1.0 to 1.9 g/cc; a tensile strength of about 1.5 to 15 kg; and a tenacity of about 10 to 40 g/tex. The fiber possess a rectangular cross-section prior to the towing operation.

Again, these measurements were made in a conventional manner. Bulk tensile strength was measured by a tensile tester, such as an INSTRON Machine of Canton, Me. In the case of sheet goods, the INSTRON machine was outfitted with clamping jaws which are suitable for securing the sheet goods during the measurement of tensile loading. The crosshead speed of the tensile tester was 25.4 cm per minute. The gauge length was 25.4 cm.

Without intending to limit the scope of the present invention, the following examples illustrate how the present invention may be made and used:

Example 1: FLOSS

A fiber of the present invention was produced in the following manner.

A fine powder PTFE resin was combined in a blender with an amount of an odorless mineral spirit (Isopar K available from Exxon Corporation) until a compound was obtained. The volume of mineral spirit used per gram of fine powder PTFE resin was 0.264 cc/g. The compound was compressed into a billet and extruded through a 0.64 mm gap die attached to a ram type extruder to form a coherent extrudate. A reduction ratio of 85:1 was used.

Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 6.0 mm widths by passing it between a set of gapped blades. The slit coherent extrudate was expanded uniaxially in the longitudinal direction over hot plates at a temperature of 325° C. at a total ratio of 30 to 1 to form a fiber. This fiber was subsequently subjected to an amorphous locking step by passing the fiber over a heated plate set at a temperature of 400° C. for about 1 second.

The fiber was then processed through the tow operation. The filament was passed over two rotating pin wheel drums which were rotating such that the contact velocity of the drums was 20% faster than the linear velocity of the filament. The filament velocity was 30 meters per minute.

The following measurements were taken on the finished fiber prior to the tow operation:

Width: 1.1 mm

Thickness: 0.089 mm

Weight/Length: 131 tex

Density: 1.34 g/cc

Tensile strength: 3600 g

Tenacity: 27.5 g/tex

Using a waxing and bobbin machine commercially available from the Cezoma BV Company, Deurne, The Netherlands, Model CE1487, a 8% by weight coating of natural beeswax and natural peppermint oil was placed on and within the towed filament. The natural beeswax containing 16% by volume of natural peppermint oil was melted to a temperature of 85° C. before being applied to the towed filament using a lick roller coating mechanism.

Example 2: TAPE

A fiber of the present invention was produced in the following manner.

A fine powder PTFE resin was combined in a blender with an amount of an odorless mineral spirit (Isopar K available from Exxon Corporation) until a compound was obtained, the volume of mineral spirit used per gram of fine powder PTFE resin was 0.264 cc/g. The compound was compressed into a billet and extruded through a 0.64 mm gap die attached to a ram type extruder to form a coherent extrudate. A reduction ratio of 85:1 was used.

Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 6.0 mm widths by passing it between a set of gapped blades. The slit coherent extrudate was expanded uniaxially in the longitudinal direction over hot plates at a temperature of 325° C. at a total ratio of 30 to 1 to form a fiber. This fiber was subsequently subjected to an amorphous locking step by passing the fiber over a heated plate set at a temperature of 400° C. for about 1 second.

The fiber was then processed through a tow operation. The filament was passed over two rotating pin wheel drums which were rotating such that the contact velocity of the drums was 20% faster than the linear velocity of the filament. The filament velocity was 30 meters per minute.

The following measurements were taken on the finished fiber prior to the tow operation:

Width: 2.2 mm

Thickness: 0.089 mm

Weight/Length: 260 tex

Density: 1.34 gram/cc

Tensile strength: 7000 grams

Tenacity: 27 g/tex

Using a waxing and bobbin machine commercially available from the Cezoma BV Company, Deurne, The Netherlands, Model CE1487, a 6% by weight coating of natural beeswax was placed on and within the towed filament. The natural beeswax was melted to a temperature of 85° C. before being applied to the towed filament using a lick roller coating mechanism.

While particular embodiments of the present invention have been illustrated and described herein, the present invention should not be limited to such illustrations and descriptions. It should be apparent that changes and modifications may be incorporated and embodied as part of the present invention within the scope of the following claims.

Having described the invention, what is claimed is:

1. An article comprising:
a dental floss having a filament material, wherein said filament material has a structure having a multitude of individual, non-continuous strands of said filament material.

2. An article comprising:
a dental-floss having a porous polytetrafluoroethylene filament material, wherein said filament material has a structure having a multitude of individual non-continuous strands of said filament material.

3. An article comprising:
a dental floss having a polymer filament material, wherein said filament material has a structure having a multitude of individual, non-continuous strands of said filament material.

4. The article of claims 1, 2, or 3 having a width of at least about 0.5 mm and a thickness at least about 35 µm.

5. The article of claims 1, 2, or 3 having a width of at least about 0.7 mm and a thickness of at least about 35 µm.

6. The article of claims 1, 2, or 3 further comprising a coating layer selected from a group consisting of: microcrystalline wax, natural beeswax, polyvinyl alcohol and polyethyleneoxide.

7. The article of claims 1, 2, or 3 further comprising at least one active ingredient selected from a group consisting of: sodium fluoride, antimicrobial, antibiotic, antibacterial agents, antifungal, dentifrice, remineralizing agents, whitening agents, immunological agents, anti-tartar, anti-caries agents, anti-plaque agents, lysozmes, anti-inflammatory agents, homeostatic agents, analgesics, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, othophosphoric acid, monosodium phosphate, monopotassium phosphate, disodium phosphate, dipotassium phosphate, hemisodium phosphate, benzothonium, chloride, acetyl trimethyl ammonium bromide, sanguinaria, triclosan, tetracycline, cety pyridinium chloride, benzothonium chloride, melt emulsion of dimethicone, flavors, natural flavor oils, dyes, and mixtures thereof.

8. The article of claims 1, 2 or 3, wherein at least one active ingredient is disposed within an interior portion of said filament material.

9. A method of producing a dental floss article comprising:

providing a filament; and towing the filament to produce a dental floss article having a structure having a multitude of individual, noncontinuous strands.

10. The method of claim 9, wherein a filament of porous polytetrafluoroethylene is provided.

11. The method of claim 9, wherein a polymeric filament is provided.

12. The method of claim 9, further comprising applying a coating to the filament.

13. The method of claim 12, wherein said coating incorporates at least one active ingredient selected from a group consisting of: sodium fluoride, antimicrobial, antibiotic, antibacterial agents, antifungal, dentifrice, remineralizing agents, whitening agents, immunological agents, antitartar, anti-caries agents, anti-plaque agents, lysozmes, anti-inflammatory agents, homeostatic agents, analgesics, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, othophosphoric acid, monosodium phosphate, monopotassium phosphate, disodium phosphate, dipotassium phosphate, hemisodium phosphate, benzothonium, chloride, acetyl trimethyl ammonium bromide, sanguinaria, triclosan, tetracycline, cety pyridinium chloride, benzothonium chloride, melt emulsion of dimethicone, flavors, natural oils, dyes and mixtures thereof.

14. The method of claim 9 further comprising winding said filament onto a spool.

15. The method of claim 14, further comprising maintaining said filament in an essentially flat orientation upon said spool.

* * * * *